United States Patent
Sathasivan et al.

(12) 
(10) Patent No.: US 6,225,105 B1
(45) Date of Patent: May 1, 2001

(54) **MUTANT ACETOLACTATE SYNTHASE GENE FROM *ARABIDOPSIS THALIANA* FOR CONFERRING IMIDAZOLINONE RESISTANCE TO CROP PLANTS**

(75) Inventors: Kanagasabapathi Sathasivan, Austin, TX (US); Norimoto Murai, Baton Rouge, LA (US)

(73) Assignee: Louisiana State University Board of Supervisors a Governing body of Louisiana State University Agricultural and Mechancial College, Baton Rouge, LA (US)

( * ) Notice: Subject to any disclaimer, the term of this patent is extended or adjusted under 35 U.S.C. 154(b) by 0 days.

(21) Appl. No.: 09/137,478

(22) Filed: Aug. 20, 1998

Related U.S. Application Data (60) Continuation of application No. 08/789,518, filed on Jan. 27, 1997, which is a division of application No. 08/363,208, filed on Dec. 22, 1994, now Pat. No. 5,767,366, which is a continuation of application No. 07/990,416, filed on Dec. 15, 1992, now abandoned, which is a continuation of application No. 07/657,429, filed on Feb. 19, 1991, now abandoned.

(51) Int. Cl.[7] ..................................................... C12N 1/20
(52) U.S. Cl. ..................................... 435/252.2; 435/252.3
(58) Field of Search .............................. 435/252.2, 252.3

(56) References Cited

U.S. PATENT DOCUMENTS 5,141,870 * 8/1992 Bedbrook et al. ................. 435/320.1

OTHER PUBLICATIONS

Sathasivan et al., Nucleic Acids Research, 18, 2188, May 1990.*

* cited by examiner

*Primary Examiner*—Rebecca E. Prouty
*Assistant Examiner*—Maryam Monshipouri
(74) *Attorney, Agent, or Firm*—Darby & Darby (57) ABSTRACT

Acetolactate synthase (ALS), a key enzyme in the biosynthesis of valine, leucine and isoleucine in plants is inhibited by herbicides comprising imidazolinones. A mutant gene encoding imidazolinone-resistant ALS has been isolated from an imidazolinone-resistant *Arabidopsis thaliana* (GH-90) and stably maintained in a plasmid pKS1. When compared with the gene coding for imidazolinone-sensitive ALS, the imidazolinone-resistant ALS gene contains a point mutation, wherein adenosine is substituted for guanosine at nucleotide 1958, resulting in the substitution of asparagine for serine at amino acid residue 653. The mutant ALS gene can be used to impart imidazolinone resistance to a crop plant; thereby permitting the utilization of the imidazolinone or analogous herbicide as a single application at a concentration which ensures the complete or substantially complete killing of weeds, while leaving the transgenic crop plant essentially undamaged.

8 Claims, 7 Drawing Sheets

FIG. 1A

```
0001  CTTGTATCCATTCTCTTAACCAATAAAAAAAGAAAGAAAGATCAATTTGATAAA

0111  ATACAATAGATAGACTAGAGATTCCAGCGTCACGTGAGTTTTATCTATAAATAA

0221  CTTCAAGTCTCATTTTTAAACAAATCATGTTCACAAGTCTCTTCTTCTTCTCTGTT

0331  CAACAACATCTTCTTCGATCTCCTTCTCCACCAAACCATCTCCTTCCTCCTCCA
        T  T  S  S  S  I  S  F  S  T  K  P  S  P  S  S  S  K
0441  TCATCCTCCTCCTCCCGCCGCCGCGGTATCAAATCCAGCTCTCCCTCCTCCAT
        S  S  S  S  R  R  R  G  I  K  S  S  S  P  S  S  I
0551  TACCAAACCCGAAACATTCATCTCCCGATTCGCTCCAGATCAACCCCGCAAGG
        T  K  P  E  T  F  I  S  R  F  A  P  D  Q  P  R  K  G
0661  ACCCTGGAGGTGCATCAATGGAGATTCACCAAGCCTTAACCCGCTCTTCCTCAA
        P  G  G  A  S  M  E  I  H  Q  A  L  T  R  S  S  S  I
0771  GCTCGATCCTCAGGTAAACCAGGTATCTGTATAGCCACTTCAGGTCCCGGAGCT
        A  R  S  S  G  K  P  G  I  C  I  A  T  S  G  P  G  A
0881  AATCACAGGACAAGTCCCTCGTCGTATGATTGGTACAGATGCGTTTCAAGAGAC
        I  T  G  Q  V  P  R  R  M  I  G  T  D  A  F  Q  E  T
0991  TTGAAGATATCCCTAGGATTATTGAGGAAGCTTTCTTTTTAGCTACTTCTGGTAGA
        E  D  I  P  R  I  I  E  E  A  F  F  L  A  T  S  G  R
1101  CCTAATTGGGAACAGGCTATGAGATTACCTGGTTATATGTCTAGGATGCCTAAAC
        P  N  W  E  Q  A  M  R  L  P  G  Y  M  S  R  M  P  K  P
1211  GCCTGTGTTGTATGTTGGTGGTGGTTGTTTGAATTCTAGCGATGAATTGGGTAGGT
        P  V  L  Y  V  G  G  G  C  L  N  S  S  D  E  L  G  R  F
1321  ATCCTTGTGATGATGAGTTGTCGTTACATATGCTTGGAATGCATGGGACTGTGTAT
        P  C  D  D  E  L  S  L  H  M  L  G  M  H  G  T  V  Y
1431  GATGATCGTGTCACGGGTAAGCTTGAGGCTTTTGCTAGTAGGGCTAAGATTGTTC
        D  D  R  V  T  G  K  L  E  A  F  A  S  R  A  K  I  V  H
1541  GTGTGGTGATGTTAAGCTGGCTTTGCAAGGGATGAATAAGGTTCTTGAGAACCGA
        C  G  D  V  K  L  A  L  Q  G  M  N  K  V  L  E  N  R
1651  AACAGAAGTTTCCGTTGAGCTTTAAGACGTTTGGGGAAGCTATTCCTCCACAGTA
        Q  K  F  P  L  S  F  K  T  F  G  E  A  I  P  P  Q  Y
1761  GTCGGGCAACATCAAATGTGGGCGGCGCAGTTCTACAATTACAAGAAACCAAGG
        V  G  Q  H  Q  M  W  A  A  Q  F  Y  N  Y  K  K  P  R
1871  TGGAGCGTCTGTTGCTAACCCTGATGCGATAGTTGTGGATATTGACGGAGATGG
        G  A  S  V  A  N  P  D  A  I  V  V  D  I  D  G  D  G
1981  TGAAGGTACTTTTATTAAACAACCAGCATCTTGGCATGGTTATGCAATGGGAAGA
        K  V  L  L  N  N  Q  H  L  G  M  V  M  Q  W  E  D
2091  GACGAGATATTCCCGAACATGTTGCTGTTTGCAGCAGCTTGCGGGATTCCAGCG
        D  E  I  F  P  N  M  L  L  F  A  A  A  C  G  I  P  A
2201  ACCAGGACCTTACCTGTTGGATGTGATTTGTCCGCACCAAGAACATGTGTTGCCG
        P  G  P  Y  L  L  D  V  I  C  P  H  Q  E  H  V  L  P
2311  TTAAATACTGAGAGATGAAACCGGTGATTATCAGAACCTTTTATGGTCTTTGTAT
        K  Y  Stop
```

```
TTTCTCAGCCACAAATTCTACATTTAGGTTTTAGCATATCGAAGGCTCAATCACAA
AGGACCAAAAATCAAATCCCGAGGGCATTTTCGTAATCCAACATAAAACCCTTAAA
TCTCTATCTCTTGCTCATCTTTCTCCTGAACCATGGCGGCGGCAACAACAACAA
                                 M  A  A  A  T  T  T  T
AATCACCATTACCAATCTCCAGATTCTCCCTCCCATTCTCCCTAAACCCCAACAAA
 S  P  L  P  I  S  R  F  S  L  P  F  S  L  N  P  N  K
CTCCGCCGTGCTCAACACAACCACCAATGTCACAACCACTCCCTCTCCAACCAAACC
 S  A  V  L  N  T  T  T  N  V  T  T  T  P  S  P  T  K  P
CGCTGATATCCTCGTCGAAGCTTTAGAACGTCAAGGCGTAGAAACCGTATTCGCTT
 A  D  I  L  V  E  A  L  E  R  Q  G  V  E  T  V  F  A  Y
TCCGTAACGTCCTTCCTCGTCACGAACAAGGAGGTGTATTCGCAGCAGAAGGATAC
 R  N  V  L  P  R  H  E  Q  G  G  V  F  A  A  E  G  Y
ACAAATCTCGTTAGCGGATTAGCCGATGCGTTGTTAGATAGTGTTCCTCTTGTAGC
 T  N  L  V  S  G  L  A  D  A  L  L  D  S  V  P  L  V  A
TCCGATTGTTGAGGTAACGCGTTCGATTACGAAGCATAACTATCTTGTGATGGATG
 P  I  V  E  V  T  R  S  I  T  K  H  N  Y  L  V  M  D  V
CCTGGACCTGTTTTGGTTGATGTTCCTAAAGATATTCAACAACAGCTTGCGATT
 P  G  P  V  L  V  D  V  P  K  D  I  Q  Q  Q  L  A  I
CTCCGGAAGATTCTCATTTGGAGCAGATTGTTAGGTTGATTTCTGAGTCTAAGAA
 P  E  D  S  H  L  E  Q  I  V  R  L  I  S  E  S  K  K
TTGTTGAGCTTACGGGGATCCCTGTTGCGAGTACGTTGATGGGGCTGGGATCTT
 V  E  L  T  G  I  P  V  A  S  T  L  M  G  L  G  S  Y
GCAAATTACGCTGTGGAGCATAGTGATTTGTTGTTGGCGTTTGGGGTAAGGTTT
 A  N  Y  A  V  E  H  S  D  L  L  L  A  F  G  V  R  F
ATATTGATATTGACTCGGCTGAGATTGGGAAGAATAAGACTCCTCATGTGTCTGT
 I  D  I  D  S  A  E  I  G  K  N  K  T  P  H  V  S  V
GCGGAGGAGCTTAAGCTTGATTTTGGAGTTTGGAGGAATGAGTTGAACGTACAGA
 A  E  E  L  K  L  D  F  G  V  W  R  N  E  L  N  V  Q  K
TGCGATTAAGGTCCTTGATGAGTTGACTGATGGAAAAGCCATAATAAGTACTGGT
 A  I  K  V  L  D  E  L  T  D  G  K  A  I  I  S  T  G
CAGTGGCTATCATCAGGAGGCCTTGGAGCTATGGGATTTGGACTTCCTGCTGCGAT
 Q  W  L  S  S  G  G  L  G  A  M  G  F  G  L  P  A  A  I
AAGCTTTATAATGAATGTGCAAGAGCTAGCCACTATTCGTGTAGAGAATCTTCCAG
 S  F  I  M  N  V  Q  E  L  A  T  I  R  V  E  N  L  P  V
TCGGTTCTACAAAGCTAACCGAGCTCACACATTTCTCGGGGATCCGGCTCAGGAG
 R  F  Y  K  A  N  R  A  H  T  F  L  G  D  P  A  Q  E
GCGAGGGTGACAAAGAAAGCAGATCTCCGAGAAGCTATTCAGACAATGCTGGATAC
 A  R  V  T  K  K  A  D  L  R  E  A  I  Q  T  M  L  D  T
ATGATCCCGAATGGTGGCACTTTCAACGATGTCATAACGGAAGGAGATGGCCGGA
 M  I  P  N  G  G  T  F  N  D  V  I  T  E  G  D  G  R  I
```

|  | 1958 |
|---|---|
| Nucleotide | Ser |
| Wild type | ATG ATC CCG AGT GGT GGC ACT TTC |
|  | I |
| Imr3 | ATG ATC CCG AAT GGT GGC ACT TTC |
|  | Asn |
| Amino acid | 653 |

FIG. 4

Control

MUTANT ACETOLACTATE SYNTHASE GENE FROM *ARABIDOPSIS THALIANA* FOR CONFERRING IMIDAZOLINONE RESISTANCE TO CROP PLANTS

This is a continuation of application Ser. No. 08/789,518, filed Jan. 27, 1997 pending which in turn is a divisional application of Ser. No. 08/363,208 filed Dec. 22, 1994 now U.S. Pat. No. 5,767,366; which in turn is a continuation of application Ser. No. 07/990,416 filed Dec. 15, 1992 abandoned; which in turn is a continuation of application Ser. No. 07/657,429, filed Feb. 19, 1991 abandoned. Each of these prior applications is hereby incorporated herein by reference, in its entirety.

FILED OF THE INVENTION

This invention relates to a mutant gene coding for imidazolinone-resistant acetolactate synthase, and the process of imparting such resistance to a plant crop.

BACKGROUND

The ability to modify microorganisms and cells of higher organisms by genetic engineering has made it possible to change certain of their specific characteristics and thereby alter the 'natural' response of those organisms to various agents. Of particular interest are the responses of organisms to agents used because of their cytotoxic effect. For example, many compounds used in agriculture are directed to the killing of pests, weeds, or the like. Often these compounds can have a relatively long residence time or extended residue in the plants subjected to treatment by the compound.

In many situations it is desirable to differentiate the species to be retained from the species to be killed. For example, it is often necessary to selectively destroy weeds, yet have minimal impact on the economically valuable crop plants. For the most part, broad-spectrum herbicides have a sufficiently adverse effect on crops that their use must be limited to emergent use or careful postemergent application.

Some weed species are simply resistant to today's herbicides, increasing the importance of developing the production of effective herbicides. Moreover, as some weed species are controlled, competition is reduced for the remaining tenacious weed species. The development of genetically engineered herbicide-resistant crop plants could significantly improve weed-control by allowing fields to be treated with a single, concentrated application of the herbicide. Therefore, a one-step procedure could eliminate costly and perhaps ineffective repeated low-dosage herbicidal treatments, such as have been required in the past to avoid damaging conventional crops, but which may have also induced the emergence of spontaneous herbicide-resistant weeds. Herbicides with greater potency, broader weed spectrum and more rapid degradation after application would avoid the problem tic persistence of the chemical herbicide in the soil, such as typically results from frequently repeated applications, and which prevents rotation of crops sensitive to that herbicide.

Certain herbicides, while not used directly to control weeds in field crops, are used: as 'total vegetation control agents' to eliminate weeds entirely in certain right-of-way or industrial situations. However, these herbicides may be deposited by natural means, such as water run-off, onto areas where economically important crops are growing. As a result sensitive field crops may be killed or their growth seriously inhibited. It is therefore highly desirable to be able to modify viable cells to make them resistant to stressful cytotoxic agents.

Sulfonylureas, imidazolinones, and triazolopyrimidines are structurally diverse, agriculturally important herbicides. Their primary target site is the enzyme acetolactate synthase (ALS), which catalyses the first common step in a plant's biosynthetic pathway of valine, leucine and isoleucine. The molecular basis of sulfonylurea resistance has been extensively characterized. Mutant forms of certain microorganisms and upper level plants expressing altered ALS resistance to sulfonylureas have been identified, i.e., in *Nicotiana tabacum* (tobacco) by Chaleff & Mauvais, *Science* 224:1443–1445 (1984), and in *Arabidopsis thaliana* by Haughn and Sommerville, *Mol. Gen. Genet.* 204:266–271 (1986). Furthermore, single amino acid substitutions in the ALS gene have been shown to confer resistance to sulfonylureas in tobacco by Lee et al., *EMBO J.* 7:1241–1248 (1988), and in Arabidopsis by Haughn et al., *Mol. Gen. Genet.* 211:266–271 (1988). However, there have been recent reports, i.e., by Sarri et al., *Plant Physiol.* 93:55–61 (1990), and Hall et al., *Plant Physiol.* 93:962–966 (1990), indicating that fields, which had been treated repeatedly with sulfonylureas have shown an emergence of herbicide-resistant biotypes of weeds which had been previously, effectively controlled.

The imidazolinone herbicides, notably imazapyr, imazaquin and imazethapyr, are a particularly important class of herbicide As described in the "Herbicide Handbook of the Weed Science Society of America", 6th Ed., (1989), imazapyr (2-[4,5-dihydro-4-methyl-4-(1-methylethyl)-5-oxo-1H-imidazol-2-yl]-3-pyridinecarboxylic acid), is a non-specific, broad-spectrum herbicide, whereas both imazaquin (2-[4,5-dihydro-4-methyl-4-(1-methylethyl)-5-oxo-1H-imidazol-2-yl]-3-quinolinecarboxylic acid), and imazethapyr (2-[4,5-dihydro-4-methyl-4-(1-methylethyl)-5-oxo-1H-imidazol-2-yl]-5-ethyl-3-pyridinecarboxylic acid) are crop-specific herbicides particularly suited to use with soybean or peanut crops. These herbicides offer low mammalian toxicity, permit low application rates to plant crops, and provide long duration broad-spectrum weed control in the treatment of agricultural crops. A crop made more resistant to imidazolinone herbicides offers a selective means to control and kill weeds without adversely affecting the crop plant.

Clearly then, an understanding of the method by which weeds become resistant to herbicides at the molecular level is essential to establishing a basis for the development of sound weed control programs. The molecular basis underlying the expression of imidazolinone-resistance had remained undetermined until the present invention.

U.S. Pat. No. 4,761,373, issued to Anderson, discloses the production of plants, plant tissues and plant seeds which are herbicide-resistant, particularly plants, plant tissues and plant seeds which exhibit resistance to such herbicides resulting from the expression of genes encoding herbicide resistant acetohydroxyacid synthase. In the patent, Anderson contemplated introducing the herbicide resistance into any agronomically important crop. However, until the present invention, neither the imidazolinone-resistant ALS gene, nor the molecular basis of the expressed activity were understood. The imidazolinone-resistance trait has proven to be transferable to other maize lines only by classical breeding techniques; but, until the current invention it has not been possible to transfer the resistance to other monocot or dicot species by genetic engineering.

Early herbicide-enzyme kinetics data by Schloss et al., in *Nature* 331:360–362 (1988), proposed that sulfonylureas, imidazolinones and trizolopyrimidines shared a common binding site on a bacterial ALS. However, additional studies by several inventors, including recent experiments by Saxena et al., *Plant Physiol.* 94:1111–1115 (1990) and Sathasivan et al., *Nucleic Acids Res.* 18:2188 (1990), have indicated that with the exception of a few cases, the mutant forms of ALS which were resistant to imidazolinone lacked cross-resistance to sulfonylureas. Therefore, identification of the mutation site(s) in the ALS gene which code for the mutant plant's imidazolinone resistance is of agricultural significance.

Furthermore, the mechanism of inhibition was shown to be dissimilar between the imidazolinone and sulfonylurea herbicides. Imidazolinones inhibit ALS activity by binding noncompetitively to a common site on the enzyme, as demonstrated by Shaner et al., *Plant Physiol.* 76:545–546 (1984). By comparison, sulfonylureas inhibit ALS activity by competition as described by La Rossa and Schloss in *J. Biol. Chem.* 259:8753–8757 (1984). Therefore, since the mechanism of action of imidazolinone appears to be different from that of sulfonylurea herbicides, understanding the molecular basis of imidazolinone resistance is of great interest.

There remains a long-felt need in the art for the isolation of a mutant ALS gene, which confers resistance to imidazolinone in higher plants, and which would provide an opportunity to introduce imidazolinone resistance into crop plants by genetic engineering. Imidazolinones, because of their broad-spectrum activity and low mammalian toxicity, are particularly suited as a type of herbicide to which genetically engineered resistance would be economically important in crop plants. The development of imidazolinone-resistant crops would provide a reliable and cost-effective alternative to conventional weed management programs.

By modifying crop plant cells by the introduction of a functional gene expressing the imidazolinone-resistant ALS enzyme, one can use imidazolinones, including imazaquin and imazapyr, or an analogous herbicide with a wide variety of crops at a concentration which ensures the substantially complete or complete removal of weeds, while leaving the crop relatively unaffected. In this manner, substantial economies can be achieved in that fertilizers and water may be more efficiently utilized, and the detrimental effects resulting from the presence of weeds avoided.

SUMMARY OF THE INVENTION

It is a primary object of this invention to provide imidazolinone-resistance, nucleic acid sequences encoding imidazolinone-resistant ALS enzymes, constructs containing the genes coding for such imidazolinone-resistant ALS enzymes under the transcriptional and translational control of regulatory genes recognized by a desired host to which the imidazolinone-resistant ALS enzyme genes are foreign, host cells containing such constructs, and organisms and organism parts or products containing such constructs.

It is an additional object of this invention to provide a gene coding for imidazolinone-resistant ALS enzymes useful in the transformation of a crop plant, and thereby effective in the protection of the host cells from the cytotoxic effect of imidazolinone.

It is also an object of this invention to provide a novel mutant ALS gene useful in the transformation of crop plants, wherein the imidazolinone resistance of the transformed crop plant is greater than that of an untreated imidazolinone-sensitive wild-type crop plant.

It is a particular object of this invention to provide a novel ALS gene capable of coding for sufficient imidazolinone resistance in a transformed crop plant that, after planting, sufficiently concentrated imidazolinone herbicide can be applied in a single treatment—to the transgenic plant crop to selectively kill substantially all of the weeds, without application of an additional herbicide.

It is a further object of this invention to increase the effectiveness of imidazolinone herbicides by producing plant crops less susceptible to damage by these herbicides when used to control weeds.

It is a further object of this invention to provide imidazolinone-resistant ALS enzyme gene constructs useful in selectively distinguishing between host cells containing the construct and host cells lacking such construct.

These and other objects are accomplished pursuant to the practice of this invention.

IN THE DRAWINGS

FIGS. 1A–1B depicts the nucleotide sequence (SEQ ID NO: 1) and amino acid sequence (SEQ ID NO: 2) of the mutant ALS gene in pKS1.

DESCRIPTION OF THE PREFERRED EMBODIMENTS OF THE INVENTION

This invention embodies the isolation of a novel mutant ALS gene from an imidazolinone-resistant plant, sequencing to identify the unique mutation, and transforming an imidazolinone-sensitive plant to confer greater imidazolinone resistance than hat originally possessed by the transformed plant.

The novel ALS gene of interest may be obtained from a higher plant, particularly a plant shown capable of resisting imidazolinone treatment. The plant can be the mutant result of various mutagenic processes, including chemical, biological, radioactive, or ultraviolet treatments. Alternatively, the imidazolinone-resistant plant can be the result of growing selected plants in soil or other medium at increasingly higher concentrations of imidazolinone until the organisms which survive have developed imidazolinone-resistant ALS enzymes. Regardless of the source of the imidazolinone-resistant organism, screening must show that the ALS gene therein effectively codes for an imidazolinone-resistant ALS enzyme.

Once one or more host strains have been identified, numerous techniques may be employed to identify the coding sequence for the imidazolinone-resistance ALS enzyme. The gene may be present on a chromosome or plasmid. The genome may be fragmented, particularly with restriction endonuclease, where one or more endonucleases may be employed to provide fragments ranging in size from less than 1 kb to about 50 kb. These fragments may be cloned on appropriate vectors in a convenient bacterium, e.g., Agrobacterium, E. coli, Neurospora, or yeast, and the resulting transformants screened for imidazolinone-resistant ALS activity, where the host organism provides a negative background.

Once one or more clones have been identified as having imidazolinone-resistant activity, the extrachromosomal elements containing the desired DNA fragment, plasmids or viruses may be isolated by conventional techniques, such as lysis of the host, precipitation of the DNA, and separation of the vector DNA, plasmid or virus DNA, from the chromosomal DNA. The extrachromosomal elements may then be cleaved by endonuclease restriction and the desired fragments isolated by various techniques for separation and identification of fragments of different sizes, e.g., electrophoresis, density gradient centrifugation, or the like.

Depending on the size of the identified fragment, it will usually be further manipulated to reduce its size to more closely approximate the size of the gene and its flanking regulatory sequences. Partial cleavage with different restriction enzymes in different reaction mixtures may be employed, followed by cloning of the fragments to determine which of the fragments still retain the ability to provide imidazolinone-resistant ALS activity.

Alternatively, the enzyme may be isolated and partially sequenced. Based on the amino acid sequence, probes can be prepared which may then be used to identify those fragments having the gene. By combining this approach with the restriction enzyme cleavage, fragments can be cloned and screened for the presence of the desired gene. In addition, one may use exonucleases, such as Bal31 to remove nucleotides from one or both ends of the fragment to further reduce the number of superfluous nucleotides.

Alternatively, the gene may be cloned in an appropriate host and messenger RNA isolated by screening with a probe, by identification in an appropriate in vitro or in vivo translation system, e.g., Xenopus oocytes or reticulolysate, or the like. Messenger RNA can be isolated as identified in the translation system and used for preparing cDNA using conventional techniques involving a reverse transcriptase and formation of the complementary chain with a DNA polymerase. In this instance, the resulting structural gene lacks the regulatory regions associated with transcription.

The gene coding for imidazolinone-resistant ALS activity may be modified in a variety of ways, truncating either or both of the 5'- or 3'-termini, extending the 5'- or 3'-termini, or the like. Usually, not more than 25, in particular not more than about 20 codons will be involved in the modification of the naturally occurring imidazolinone-resistant ALS gene. The gene may be extended by as many as 50 amino acids, usually not more than about 30 amino acids. Combinations of substitution, truncation and extension may be employed. Thus the gene may be manipulated in a variety of ways to change the characteristic of the enzyme, for convenience in manipulation of the plasmids, or the like. Once the molecular basis of imidazolinone-resistance is known, similar mutations could be introduced into other plant ALS genes to obtain imidazolinone-resistance.

The DNA sequence containing the structural gene expressing the imidazolinone-resistant ALS may be joined to a wide variety of other DNA sequences for introduction into an appropriate host cell. The companion sequence will depend upon the nature of the host, the manner of introduction of the DNA sequence into the host, and whether episomal maintenance or integration is desired.

For prokaryotic hosts, a wide variety of vectors exist which may be used for introduction by transformation conjugation, transduction or transfection of the DNA sequence into a prokaryotic host. DNA vector include a wide variety of plasmids, such as pBR322, pMB9, and the like; cosmids, such as pVK100; or viruses such as P22, and the like.

For eukaryotic hosts, a wide variety of techniques may be employed for DNA introduction into the host, such as transformation with $Ca^{++}$-precipitated DNA, involving a non-replicating DNA sequence, a plasmid or a minichromosome, transformation, microinjection with a micropipette, electroporation, polyethylene glycol (PEG) mediated transformation of protoplasts, or gene gun or particle bombardment techniques.

Whether the DNA may be replicated as an episomal element, or whether the DNA may be integrated into the host genome and the structural gene expressed in the host, will be determined by the presence of a competent replication system in the DNA construction. Episomal elements may be employed, such as tumor inducing plasmids, e.g., Ti or Ri, or fragments thereof, or viruses, e.g., CaMV, TMV or fragments thereof, which are not lethal to the host, and where the structural gene is present in such episomal elements in a manner allowing for expression of the structural gene. Of particular interest are fragments having the replication function and lacking other functions such as oncogenesis, virulence, and the like.

To introduce isolated genes or groups of genes into the genome of plant cells an efficient host gene vector system is necessary. The foreign genes should be expressed in the transformed plant cells and stably transmitted, somatically or sexually to a second generation of cells produced. The vector should be capable of introducing, maintaining, and expressing a gene from a variety of sources in the plant cells. Additionally, it should be possible to introduce the vector into a variety of plants, and at a site permitting effective gene expression. Moreover, to be effective, the selected gene must be passed on to progeny by normal reproduction.

The fragments obtained from the imidazolinone-resistant source may be cloned employing an appropriate cloning vector. Cloning can-be carried out in an appropriate unicellular microorganism, e.g., a bacterium, such as E. coli, or Salmonella. In particular, one may use a phage, where partial or complete digestion provides fragments having about the desired size. For example, the phage lambda may be partially digested with an appropriate restriction enzyme and ligated to fragments resulting from either partial or complete digestion of a plasmid, chromosome, or fragment thereof. Packaging will insure that only fragments of the desired size will be packaged and transduced into the host organism.

The host organism may be selected for ALS activity. The recipient strains may be modified to provide for appropriate genetic traits which allow for selection of transductants. In microorganisms, the transductants may be used for conjugation to other microorganisms, using a mobilizing plasmid as required. Various techniques may be used for further reducing'the size of the fragment containing the structural gene for the imidazolinone-resistant ALS activity. For example, the phage vector may be isolated, cleaved with a variety of restriction endonucleases, e.g., EcoRI, BamHI, and the like, and the resulting fragments cloned in an appropriate vector, conveniently the phage vector previously used. Instead of a phage vector, a variety of cloning vectors are available of suitable size.

Desirably, the fragment including flanking regions will be about 11.5 kb. Of particular interest is a XbaI fragment from *Arabidopis thaliana*. More particularly the subcloned fragment is about 5.8 kb; specifically the gene is about 2.1 kb.

The imidazolinone-resistant ALS enzyme may be expressed by any convenient source, either prokaryotic or eukaryotic, including bacteria, yeast, filamentous fungus, plant cells, etc. Where secretion is not obtained, the enzyme may be isolated by lysing the cells and isolating the mutant ALS according to known ways. Useful ways include chromatography, electrophoresis, affinity chromatography, and the like.

The DNA sequence encoding for the imidazolinone-resistant ALS activity may be used in a variety of ways. The DNA sequence may be used as a probe for the isolation of mutated or wild type ALS sequences. Also saturation or site-directed mutagenesis could be performed on a plant ALS gene to select for mutants expressing greater levels of herbicide-resistance, as well as resistance to more classes of herbicide. Alternatively, the DNA sequence may be used for integration by recombination into a host to provide imidazolinone resistance in the host. The mutant ALS gene can also be used as selection marker in the plant transformation experiments using the imidazolinone herbicide as the selection agent.

With plant cells, the structural gene as part of a construction may be introduced into a plant cell nucleus by micropipette injection for integration by recombination into the host genome. Alternatively, methods including electroporation, polyethylene glycol (PEG) mediated transformation of protoplasts, or gene gun or particle bombardment techniques may be employed for introduction of the structural gene into a plant host cell. Where the structural gene has been obtained from a source having regulatory signals which are not recognized by the plant host, it may be necessary to introduce the appropriate regulatory signals for expression. Where a virus or plasmid, e.g., tumor inducing plasmid, is employed and has been mapped, a restriction site can be chosen which is downstream from a promoter into which the structural gene may be inserted at the appropriate distance from the promoter. Where-the DNA sequences do not provide an appropriate restriction site, one can digest for various times with an exonuclease, such as Bal31 and insert a synthetic restriction endonuclease site (linker).

Of particular interest is the use of a tumor-inducing plasmid, where the imidazolinone-resistant ALS gene may be integrated into plant cell chromosomes, e.g., Matzke et al., *J. Mol. App. Genetics* 1:39–49 (1981). Directed genetic modification and expression of foreign genes in dicotyledons (broad-leaf plants) such as tobacco, alfalfa, etc. has been shown to be possible using the T-DNA of the Ti plasmid of *Agrobacterium tumefaciens*. Following genetically engineered insertion of a foreign DNA fragment into T-DNA in Agrobacterium, the host plant can be transfected by the bacterium or Ti plasmid, thus inserting the foreign DNA into the host plant chromosome to eventually produce a genetically engineered plant. Alternatively Ri, or e root-inducing, plasmids may be used as the gene vectors.

Although Agrobacterium effectively transform only dicots, the Ti plasmid permits the efficacious manipulation of the bacteria to act as vectors in monocotyledonous crop plants, i.e., wheat, barley, rice, rye, etc. Alternatively, Ti plasmids or other plasmids may be introduced into the monocots by artificial methods such as microinjection, or fusion between the monocot protoplasts and bacterial spheroplasts containing the T-region which could then be integrated into the plant nuclear DNA.

By employing the T-DNA right border, or both borders, where the borders flank an expression cassette comprising the imidazolinone-resistant ALS structural gene under transcriptional and translational regulatory signals for initiation and termination recognized by the plant host, the expression cassette may be integrated into the plant genome and provide for expression of the imidazolinone-resistant ALS enzyme in the plant cell at various stages of differentiation. Various constructs can be prepared providing for expression in plant cells.

To provide for transcription, a variety of transcriptional initiation regions (promoter regions), either constitutive or inducible, may be employed. The transcriptional initiation region is joined to the structural gene encoding the imidazolinone-resistant ALS activity to provide for transcriptional initiation upstream from the initiation codon, normally within about 200 bases of the initiation codon, where the untranslated 5'-region lacks an ATG. The 3'-end of the structural gene will have one)or more stop codons which will be joined to a transcriptional termination region functional in a plant host, which termination region may be associated with the same or different structural gene as the initiation region.

The expression cassette is characterized by having the initiation region, the structural gene under the transcriptional control of the initiation region, and the termination region providing for termination of transcription and processing of the messenger RNA, in the direction of transcription as appropriate.

Transcriptional and translational regulatory regions, conveniently tml promoter and terminator regions from *A. tumefaciens* may be employed, which allow for constitutive expression of the imidazolinone-resistant ALS gene. Alternatively, other promoters and/or terminators may be employed, particularly promoters which provide for inducible expression or regulated expression in a plant host. Promoter regions which may be used from the Ti-plasmid include opine promoters, such as the octopine synthase promoter, nopaline synthase promoter, agropine synthase promoter, mannopine synthase promoter, or the like. Other promoters include viral promoters, such as CaMV Region VI promoter or full length (35S) promoter, the promoters associated with the ribulose-1,5-bisphosphate carboxylase genes, e.g., the small subunit, genes associated with phaseolin, protein storage, B-conglycinin, cellulose formation, or the like.

The various sequences may be joined together in conventional ways. The promoter region may be identified by the region being 5' from the structural gene, for example, the tml gene, and may be selected and isolated by restriction mapping and sequencing. Similarly, the terminator region may be isolated as the region 3' from the structural gene. The sequences may be cloned and joined in the proper orientation to provide for constitutive expression of the imidazolinone-resistant ALS gene in a plant host.

The expression cassette expressing the imidazolinone-resistant ALS enzyme may be introduced into a wide variety of plants, both monocotyledon and dicotyledon, including maize, wheat, soybean, tobacco, cotton, tomatoes, potatoes, Brassica species, rice, peanuts, petunia, sunflower, sugar beet, turfgrass, etc. The gene may be present in cells or plant parts including callus, tissue, roots, tubers, propagules, plantlets, seeds leaves, seedlings, pollen, or the like.

By providing for imidazolinone-resistant plants, a wide variety of formulations may be employed for protecting crops from weeds, so as to enhance crop growth and reduce competition for nutrients. The mutant ALS gene can be introduced into plants, preferably crop plants, most preferably into tobacco, and regenerated to produce a new family of transgenic plants which possess increased resistance to imidazolinone as compared with that possessed by the corresponding wild plants. An imidazolinone, such as imazapyr, could be used by itself for postemergence control of weeds with transgenically protected crops, such as sunflower, soybeans, corn, cotton, etc., or alternatively, in combination formulations with other products. For example, the introduction of the mutant ALS gene into *Nicotiana tabacum* var. *Xanthi* using *Agrobacterium tumefaciens* via leaf disc co-cultivation method confers resistance to the imidazolinone herbicide imazapyr at least up to about one hundred times, in particular up to one thousand times that of the wild plant.

Formulations could include other additives, such as detergents, adjuvants, spreading agents, sticking agents, stabilizing agents, or the like. The formulations may either be wet or dry preparations, including flowable powders, emulsifiable concentrates and liquid concentrates, such as are known in the art.

The herbicidal solutions may be applied in accordance with conventional methods, for example, by spraying, irrigation, dusting, or the like.

The following is further exemplary of the invention, and specifically defines preferred techniques for the production of an imidazolinone herbicide resistant *Arabidopsis thaliana*, acetolactate synthase gene, process for conferring imidazolinone herbicide resistance to plants other than *Arabidopsis thaliana*, and imidazolinone herbicide resistant transgenic plants.

The following examples are offered by way of illustration and not by way of limitation.

EXAMPLES

A novel ALS gene can be isolated from the mutated *Arbidopsis thaliana*. The mutant plant prior to separation of the ALS gene is many more times (100x) resistant to a imidazolinone herbicide than the wild plant. A genomic DNA library was thus constructed from the herbicide resistant mutant GH-90 DNA, in the lambda vector EMBL3 and screened by an ALS gene probe. One of three positively hybridizing clones was selected containing the ALS gene and purified. The ALS gene was subcloned as a 5.8 kb XbaI fragment in pUC18 and in pBluescriptKS+. Nested deletions were created using Exonuclease III and Mung bean nuclease treatment. Missing regions were subcloned in pBluescriptKS+. The DNA sequence was determined by both double and single stranded sequencing techniques using the dideoxy chain termination method. The mutant ALS gene, as contrasted with the unmutated imidazolinone-sensitive ALS gene, contains a point mutation from guanosine to adenosine at nucleotide 1958 of the ALS coding sequence, resulting in a substitution of serine to asparagine at amino acid residue 653; a unique mutation closest to the carboxyl terminal of the enzyme.

The mutant ALS gene can be introduced into imidazolinone-sensitive plants other than *Arabidopsis thaliana*, preferably crop plants, and regenerated to produce a new family of imidazolinone-resistant plants.

Materials and Methods

Restriction enzymes and T4 ligase for ligations were utilized according to manufacturer's recommendations. Standard methods in cloning and molecular analysis were performed according to Maniatis et al., (1982) *Molecular Cloning: A Laboratory Manual*, Cold Spring Harbor Laboratory, New York.

*Agrobacterium tumefaciens* strain LBA4404 was used for the plant transformation experiments. Agrobacterium mediated plant transformation and regeneration of transgenic plants was according to the method of Burow et al., *Plant Mol. Biol. Reporter* 8:124–139 (1990), and utilized media formulations, co-cultivation growth and selection conditions disclosed therein.

The imazapyr-resistant *Arabidopsis thaliana*, referred to as GH-90, and used for all cloning experiments, as well as pGH1 from which the corresponding nucleotide probes were derived, were obtained from Drs. George W. Haughn and Chris R. Somerville of Michigan State University, East Lansing, Mich. The isolation, genetic analysis and characterization of the GH-90 mutant plant are detailed by Haughn and Sommerville in *Plant Physiol.* 92:1081–1085 (1990). Briefly, GH-90 was found to be approximately 100-fold more resistant to imazapyr than wild type control plants. However, the mutant, GH-90, was neither resistant to sulfonylureas nor triazolopyrimadines. Genetic analyses have indicated a single dominant nuclear mutation in a locus designated imr.

The procedure employed in isolating the ALS gene from the mutant *Arabidopsis thaliana* plant, analysis and identification of the ALS gene, and the introduction of the ALS gene into *Nicotiana tabacum* var. *Xanthi* using *Agrobacterium tumefaciens* via a leaf disc co-cultivation method to confer resistance to the herbicide imazapyr is described as follows.

GH-90 Plant DNA Isolation

The total DNA from *Arabidopsis thaliana* wild type and GH-90 was isolated according to the method of Leutwiler et al, *Mol. Gen. Genet.* 194:15–34 (1984), with some modifications. Approximately 10 g of Arabidopsis plants were rinsed with water, frozen with liquid nitrogen, and ground by mortar and pestle. The powder was mixed with 100 ml of extraction buffer containing 150 mM Tris HCl (pH 8.5), 100 mM EDTA, 2% N-lauryl sarcosine and 10 mg proteinase K (freshly added). After incubation at 37° C. for 30 min, the mixture was centrifuged at 10,000×G for 10 min at 4° C. The supernatant was filtered through sterile cheese cloth and centrifuged again to remove'the residues. The supernatant was mixed with two volumes of ethanol and 0.1 volume of 3.0 M sodium acetate to precipitate the nucleic acids. The supernatant was removed and the pellet resuspended in 16 ml of 10 mM Tris (pH 8.0), 1 mM EDTA. Using standard procedures, the DNA band was isolated by CsCl density centrifugation, followed by dialysis. The DNA quality was assessed by both spectrophotometer and agarose gel electrophoresis.

Southern Blot Hybridization Analysis of the Genomic GH-90 DNA

The purified DNA was completely digested with EcoRI and XbaI restriction endonuclease enzymes, then fractionated by electrophoresis over an 0.8% agarose gel, along with copy number controls. The fractionated DNA was transferred to nitrocellulose filters (Schneider and Schull) for Southern blot hybridization analysis, performed according to the method of Southern et al., *J. Mol. Biol.* 98:503–517 (1985). The bound DNA was hybridized to $^{32}$P-labeled 2.1 kb and 2.4 kb EcoRI probes containing the 5'- and 3'-regions respectively of the ALS gene from pGH1.

Construction and Screening of the Genomic DNA Library

The small genome size of Arabidopsis and the availability of a homologous ALS gene probe facilitated the cloning and characterization of the ALS gene from GH-90. Briefly, a genomic DNA library was constructed from the GH-90 DNA, termed imr3 for the purposes of this example, in the lambda vector EMBL3 and screened by the oligolabeled ALS gene probe derived from pGH1. [The library construction and screening were basically as described by Kaiser and Murray in "DNA Cloning: A Practical Approach", Vol. 1; (ed., Glover); IRL Press Ltd, Oxford, England (1985).] The method used is described in greater detail as follows.

The DNA from the GH-90 mutant was partially digested by Sau3A, then size selected by sucrose density gradient centrifugation. Fragments of approximately 15–20 kb were pooled.

The phage vector EMBL3 DNA was self ligated, digested with BamHI and the central fragment was removed. The EMBL3 arms and the 15–20 kb pooled fragments from imr3 were ligated and packaged using an in vitro packaging kit from Promega Biotec, according to manufacturer's directions. It was determined by standard methods that the library contained approximately $3.2 \times 10^4$ plaque forming units/ml, which was sufficient to screen for a single copy gene with 99% probability.

The library was plated onto *E. coli* strain K803 and probed with 2.1 kb and 2.4 kb EcoRI fragments, representing the 5'- and 3'-regions respectively of the ALS gene from pGH1. After screening 32,000 plaques from the GH-90 genomic DNA library, three positively hybridizing clones were identified. From the three identified clones, the first one, designated imr3ALS3, was selected for further purification by screening two more times with the same probes. The DNA of the selected phage imr3ALS3 was isolated and separately hybridized to the 5' and 3' ALS probes.

The imr3ALS3 isolate was mapped by restriction enzyme analysis. The results indicated that the complete ALS gene had been cloned within a 11.5 kb insert of imr3ALS3, as shown in the restriction map of the clone in FIG. 2A. The restriction sites in the coding and surrounding regions of the gene were essentially identical to the wild type except that there was an additional ClaI site approximately 1.2 kb in the 5' direction upstream from the ALS coding sequence.

Subcloning and Sequencing

Figure 2A:
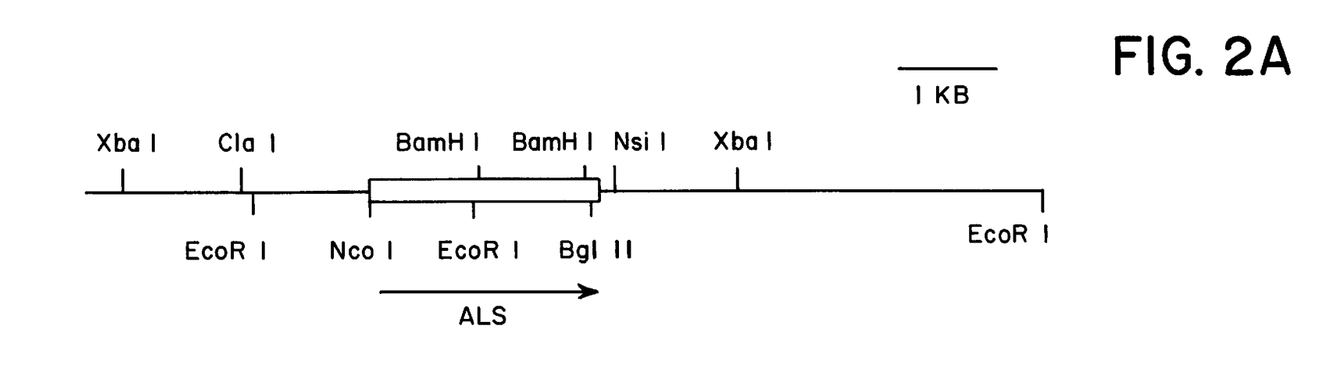
FIG. 2A depicts the restriction endonuclease map of aid part of the lambda clone, including the mutant gene encoding imidazolinone-resistant ALS.
Figure 2B:
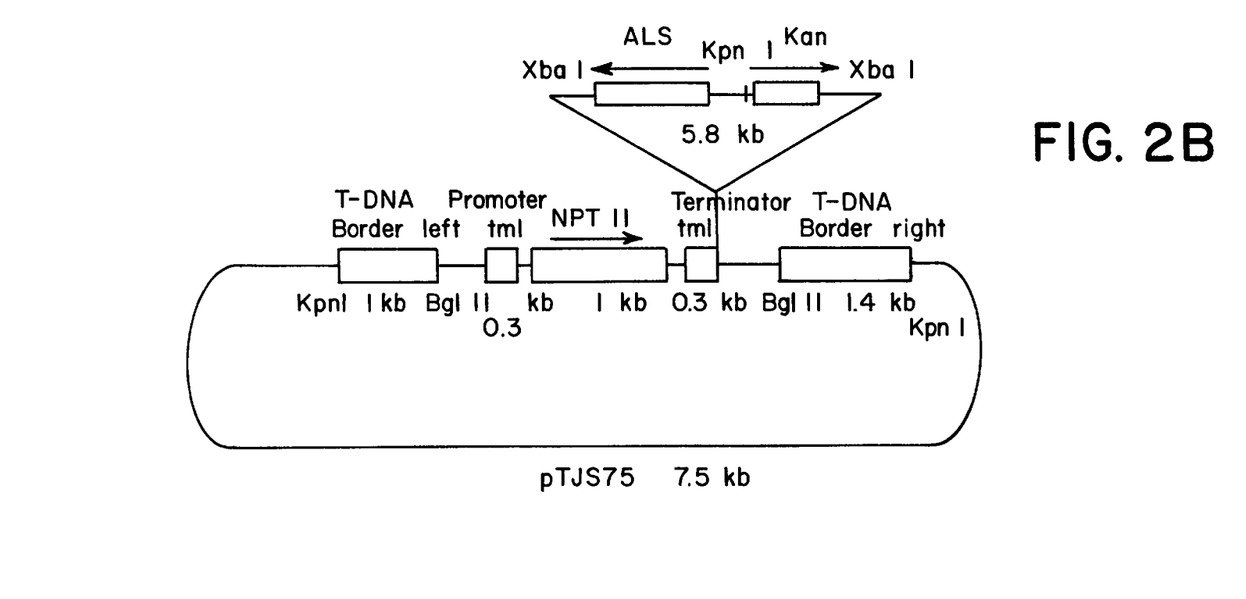
FIG. 2B depicts the construction of pTRA435, the plant transformation vector containing the mutant ALS gene.

The ALS gene subcloning and sequencing strategy is shown in FIG. 2. Specifically, a 5.8 kb XbaI fragment from imr3ALS3, containing the ALS gene and its flanking sequences, was subcloned into a pUCl8 vector. The plasmid was designated pKS1. The same fragment was also subcloned into pBluescriptKS+. The correct orientation was confirmed in each case. For comparison, a 4.6 kb Xbal/ClaI fragment was subcloned into pBluescriptKS+in the opposite orientation.

Nested deletions of the pBluescript clones were created using Exonuclease III and Mung bean nuclease as described in the Stratagene instruction manual, "Exo/Mung-DNA Sequencing". The nested deletions were ascertained by dsDNA sequencing, performed according to the Sanger dideoxy sequencing method (*Proc. Natl. Acad. Sci. U.S.A.*, 74:5463–5467 (1977)), with $^{35}$S-dATP and buffer gradient gels (Biggins et al., *Proc. Natl. Acad. Sci. U.S.A.*, 80:3963–3965 (1983)). The missing regions were separately cloned into pBluescriptKS+ and sequenced using single stranded sequencing according to the same chain termination method.

The DNA sequence was analyzed by a DNA Sequence Analysis Software program written by Niegal, University of Louisiana, Lafayette, La. Both of the DNA strands of the mutant ALS gene were sequenced from 300 bp upstream to 30 bp downstream from the coding region. The entire DNA sequence of the mutant ALS gene is shown as FIGS. 1A–1B.

Figure 3A:
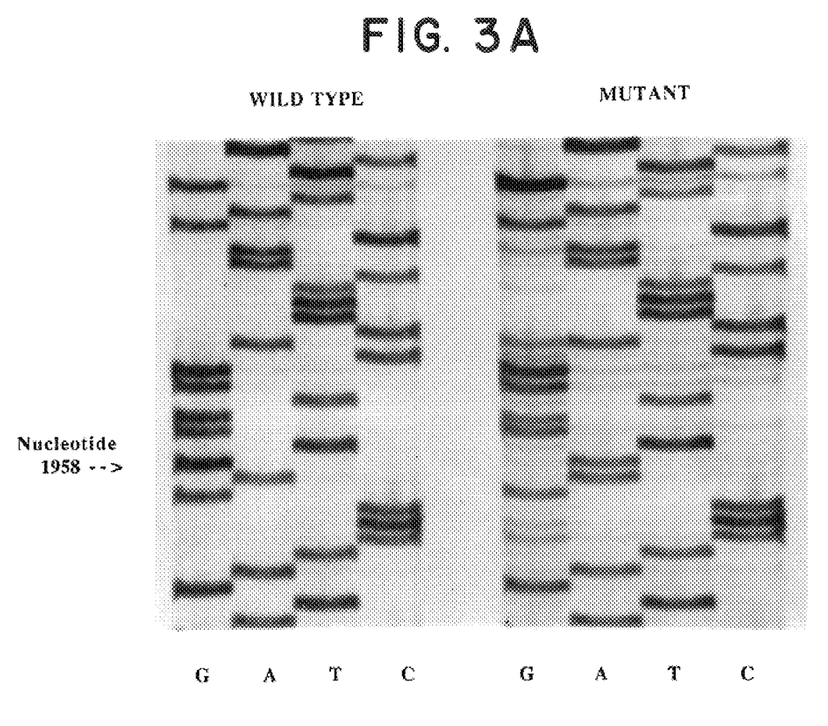
FIGS. 3A–3B depict a single point mutation from G to A in the ALS gene at nucleotide 1958, shown by:
(A) a comparison of the 6% polyacrylamide sequencing gels of the pBluescriptKS+ subcloned Bgl II/Nsi I fragment at the 3' region of the mutant ALS gene and the wild type ALS gene, and
(B) a graphic comparison of the mutant ALS nucleotide (imr3) and the wild type sequences at the mutation site.
Figure 3B:
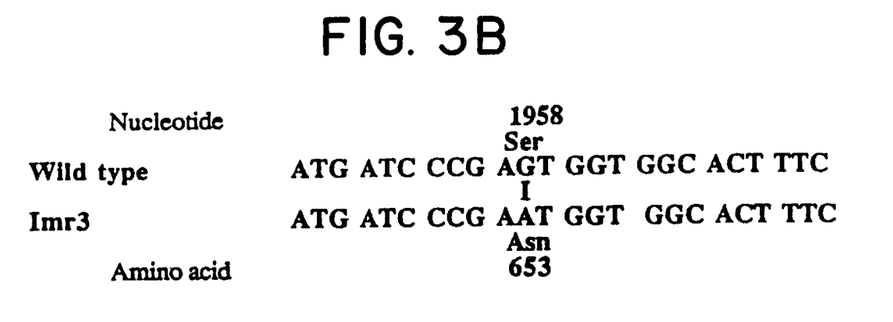

A single point mutation from G to A was identified at nucleotide 1958 of the ALS coding sequence, see FIG. 3A. As a result of the point mutation in the ALS gene, asparagine (Asn) is substituted for serine (Ser) at amino acid residue 653, nearest the carboxyl terminal of the wild type mature ALS protein. The ALS mutation is unique to the imidazolinone-resistant *Arabidopsis thaliana*, and unlike the mutations conferring for sulfonylurea resistance, as reported by Lee et. al., *EMBO J.* 7:1241–1248 (1988), and by Haughn et al., *Mol. Gen. Genet.* 211:266–271 (1988).

A point mutation could cause changes in the secondary structure, minor alterations in the herbicide binding site or an altered electrical charge. Probably the identified point mutation alters the enzyme-herbicide interaction site, thus interfering with the ability of imidazolinone to bind to ALS.

Plant Transformation

The mutant ALS gene, imr3ALS3, was introduced into *Nicotiana tobacium* var. *Xanthi* using *Agrobacterium tumefaciens* via tobacco leaf disc co-cultivation methods as described.

The pTRA409 binary plant transfection vector was selected from the pTRA400 series vectors developed by Chlan and Murai, *J. Cell. Biochem.* S13D:298 (1989) and by Lee and Murai, *Plant Physiol.* 90S:192 (1989). The pTJS75-derived vectors contain a bacterial-expressible tetracycline resistance gene. The pTRA409 vector is further comprised of the plant-expressible NPTII gene under the regulatory control of the tml promoter and terminator, derived from *A. tumefaciens* pTi15955, together with the T-DNA left and right border fragments (Hoekema et al., *Nature* 303:179–180 (1983)). The NPTII is a gene expressed in plants which provides kanamycin resistance to the construction, and thereby provides a positive selection marker. The vector was digested with XbaI, then the ends were dephosphorylated with calf intestinal alkaline phosphatase.

The 5.8 kb XbaI fragment, containing the ALS gene and a kanamycin prokaryotic selection marker, was ligated with the pTRA409 vector to generate the expression vector cassette pTRA435, as shown in FIG. 2B. Cloning a fragment of 5.8 kb in an 11.5 kb vector proved difficult without the additional kanamycin selection marker (Kan). The prokaryotic kanamycin resistance fragment was derived from $_K$SAC (a commercially available construction of a pUC vector and kanamycin resistant gene delivered by transposon Tn903).

The pTRA435 containing the mutant ALS gene was introduced into Agrobacterium tumefaciens strain LBA4404 by freeze-thaw methods. Then, the transformed Agrobacterium were introduced into tobacco leaf discs by co-cultivation, as described by Burow et al. in *Plant Mol. Biol. Reporter* 8:124–139 (1990). Leaf disc transformants were selected by screening with 300 mg/l kanamycin and 500 mg/l carbenicillin. Forty-two independent transformants were selected and propagated on shooting media. Notably, the kanamycin concentration was reduced in the secondary selection since selective pressure was no longer necessary. The transformants which rooted in kanamycin (100 mg/l) containing media were used for further analysis.

The primary and secondary selection of the transformants was based on the kanamycin resistance conferred on the expression vector by the co-transformed NPTII gene. The herbicide imazapyr was not used as the selection agent. This precluded the chances of picking up spontaneous mutants resistant to the herbicide.

Evaluation of Herbicide Resistance in the Transformed Plants

Figure 4:
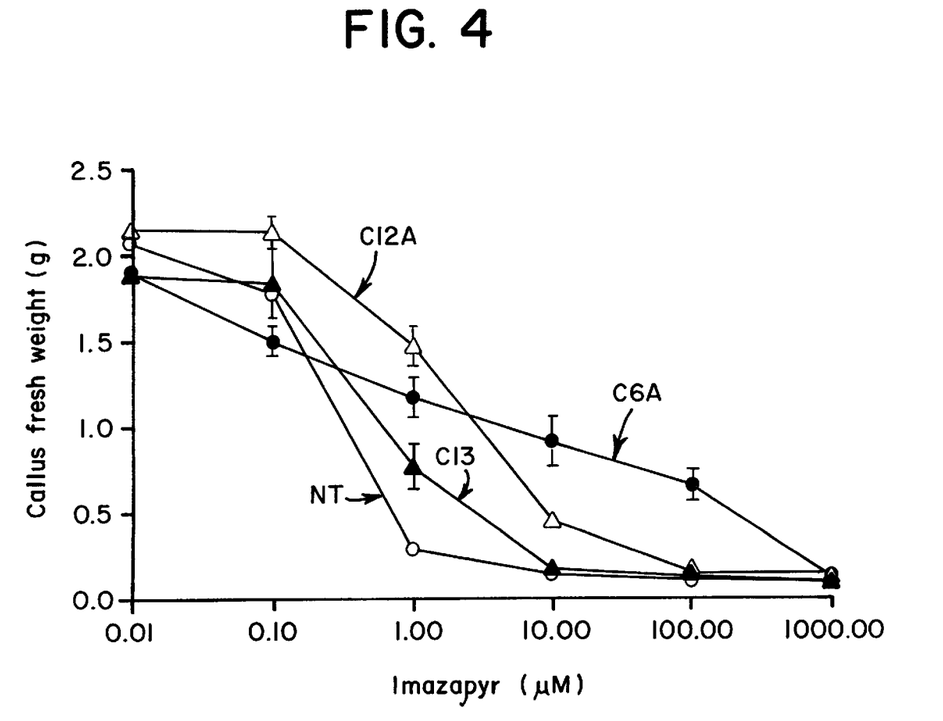
FIG. 4 is a graphical expression of imazapyr-resistance in transformed *N. tabacum* calli derived from the independently transformed leaf discs 435-6A, 435-12A, and 435-13, grown with non-transformed control (NT) in various concentrations of imazapyr for 21 days before measuring the fresh weight.
Figure 5A:
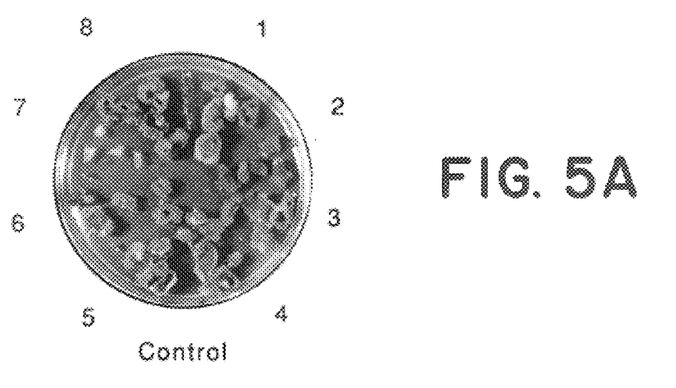
FIGS. 5A–5E depict by photograph the expression of imazapyr-resistance in tobacco plant leaf cuttings of non-transformed (1), and the regenerated transformants 435-3A (2), 435-6B (3), 435-8A (4), 435-8D (5), 435-9B (6), 435-11A (7), and 435-12A (8) following 21 days cultivation on callus maintenance media with various imazapyr concentrations.
Figure 5B:
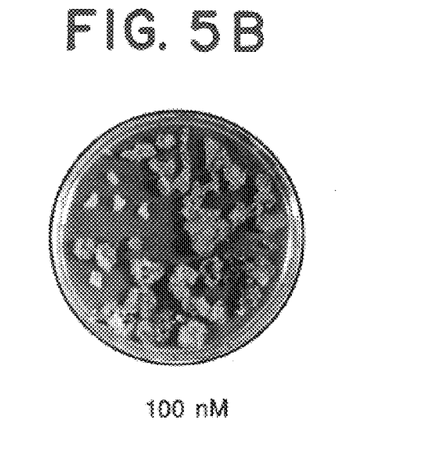
Figure 5C:
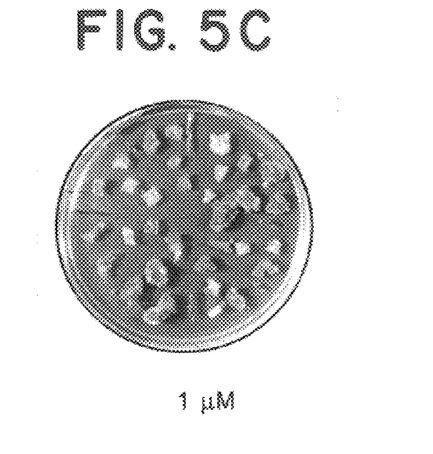
Figure 5D:
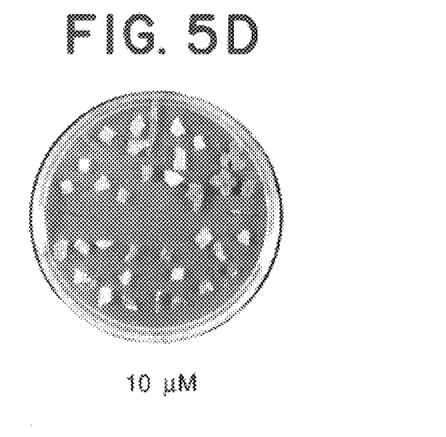
Figure 5E:
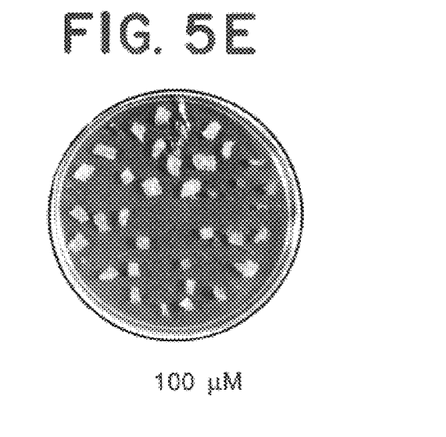

To confirm the expression of herbicide resistance, the transgenic calli derived from the independently transformed leaf discs 435-6A, 435-12A, and 435-13 and the non-transformed control were plated on callus maintenance media containing different concentrations of the imazapyr. The imazapyr was dissolved in sterile 10 mM potassium phosphate buffer to make a 50 mM stock, then and the stock was diluted to make the desired concentration. Each treatment had four replications and the experiment was repeated three times., The non-transformed control calli grew in concentrations only up to 100 nM of imazapyr. As diagramed in FIG. 4, the transformants 435-6A, 435-12A, and 435-13 survived and grew in the herbicide concentrations up to 100 $\mu$M, 10 $\mu$M, and 1 $\mu$M imazapyr, respectively, showing 1000-, 100- and 10-fold resistance to the non-selective herbicide imazapyr. The fact that the growth of the non-transformed calli was greater than that of the transformants in the non-selective media without herbicide suggested that the resistance to imazapyr is due to the modified enzyme and not due to a higher growth rate.

The variation in the levels of resistance could be due to the position, and number of copies of the introduced mutant ALS gene into the genome of the transformed calli. Moreover, as these calli were derived from the independent leaf discs after the secondary selection, they were mixture of several transformed cells. Hence to confirm that the resistance is expressed at the whole plant level, the following experiment was performed.

Expression of Imazapyr-resistance in the Transgenic Plant Leaf

To prove that the whole plants regenerated from a single transformed cell with the mutant ALS gene are resistant to imidazolinones, the leaf cuttings of the transformed and non-transformed plants were surface sterilized and placed on the callus maintenance medium containing various concentrations of imazapyr. In addition to herbicide, the media contained 500 mg/l carbenicillin to suppress the growth of any residual Agrobacterium. The herbicide was prepared as previously described. The experiment was conducted twice with four replications per treatment.

As seen in FIG. 5 the non-transformed control leaf survived and formed callus up to the imazapyr concentration of 100 nM and was killed at 1 $\mu$M. The transformant 435-3A survived up to 10 $\mu$M, showing 100-fold resistance at the plant leaf level. The transformants 435-8A and 435-8D showed only 10-fold resistance by surviving up to 1 $\mu$M imazapyr. The presence of introduced ALS gene in the transformant 435-3A showing maximum resistance has been confirmed by Southern hybridization analysis.

The variation in the levels of resistance could be due to the position, rearrangement and number of copies of the introduced mutant ALS gene in genome of the transformed calli. Furthermore, the surface sterilization treatment with bleach and Triton X-100 also increased the phytotoxicity of the herbicide. The transformants which did not exhibit a level of imidazolinone-resistance greater than or equal to that of the control could have been disadvantageously effected by the surface sterilization or rearrangement of the mutant ALS gene to give incomplete enzyme or due to lack of the introduced gene (since the selection agent was kanamycin). However, the level of imazapyr resistance at the whole plant level of pTRA 435-3A and 435-8A, showing imazapyr resistance, were well correlated with the levels of resistance at the enzyme level as shown below.

Acetolactate Synthase Assay

Activity of ALS was measured based on the method described by Chaleff et al., *Science* 224:1443–1445 (1984), and as modified by Haughn et al., *Plant Physiol.* 92:1081–1085 (1988) and by Singh et al., *Analy. Biochem.* 171:1173–179 (1988).

Three grams of fresh leaf or calli samples were ground to a fine powder in liquid nitrogen. The powder was mixed in 10 ml cold extraction buffer containing 100 mM phosphate buffer pH 7.5, 10 mM MgCl$_2$, 40 mM sodium pyruate, 500 $\mu$M thiamine pyrophosphate, 23 mM FAD (flavoadenine dinucleotide), and 1% polyvinyl pyrolidone. The homogenate was passed through sterile cheese cloth or the like to remove particulate matter, then centrifuged at 27,000×G. at 4° C. for 10 min. The supernatant was aliquoted into 200 $\mu$l volumes in Eppendorf tubes. Fifty $\mu$l of a 10× herbicide concentration, and 250 $\mu$l of a 2× assay buffer (65 mM potassium phosphate, pH 7.5, 10 mM MgCl$_2$, 100 mM sodium pyruate, 250 $\mu$M thiamine pyrophosphate, and 23 mM FAD) were added to each aliquot. The reaction mixture was incubated at 37° C. for 90 min. The conversion of acetolactate to acetoin and the measurement of acetoin were as described in 1984 by Chaleff et al., supra.

Figure 6:
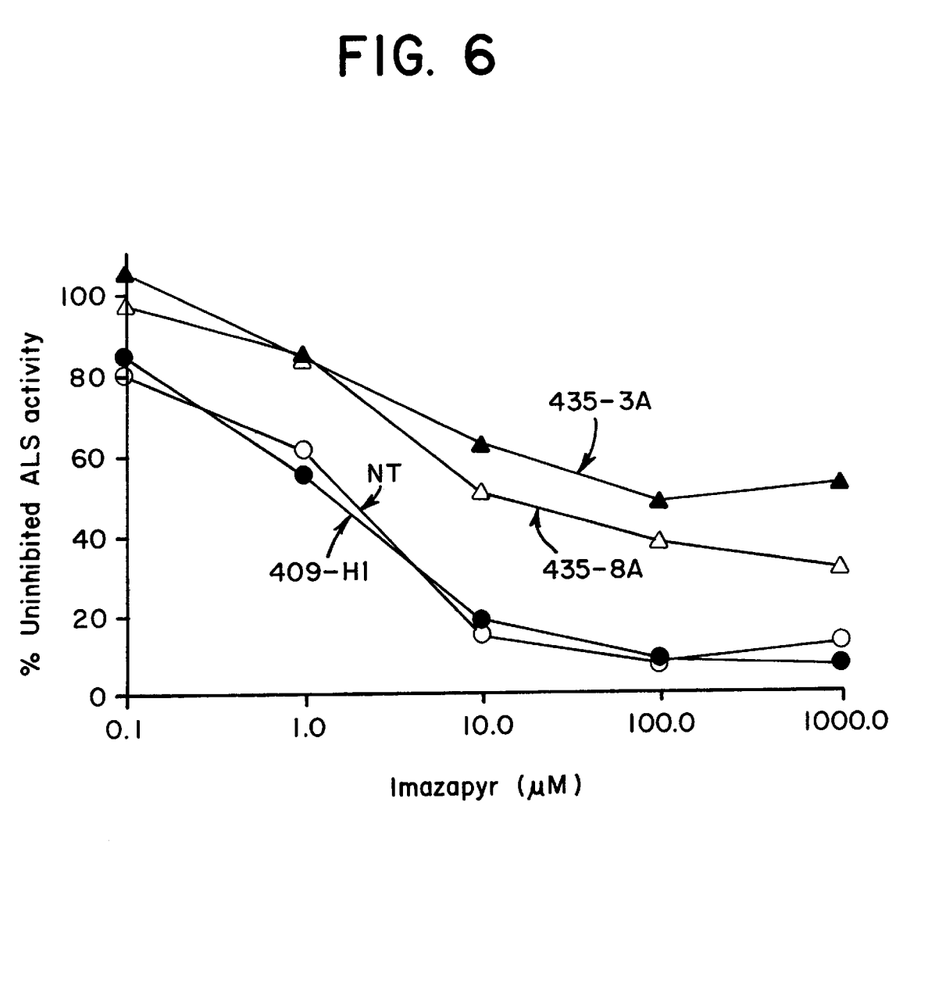
FIG. 6 graphically illustrates an assay of acetolactate synthase activity in tobacco leaf extracts, wherein ALS activity was expressed as percentage of control without any herbicide in crude leaf extracts which were non-transformed (NT), transformed with vector only (409-HI), or transformed with the expression cassette containing the mutant ALS gene (435-3A and 435-8A).

The crude leaf extracts as prepared above, were used for enzyme inhibition studies utilizing imazapyr concentrations of 1 mM, 100 $\mu$M, 10 $\mu$M, 1 $\mu$M, 100 $\mu$M, as prepared above. As seen in FIG. 6, the ALS activity in the non-transformed plants was completely inhibited (100%) at a imazapyr concentration of 10 $\mu$M. By comparison at the same 10 $\mu$M imazapyr concentration, the ALS inhibition, in transformants 435-3A and 435-8A, declined to approximately 50% of the control. The 50% inhibition of ALS activity may be accounted for by the fact the transformed plants are heterozygous for both the endogenous wild type ALS and mutant imidazolinone-resistant ALS.

A substantially constant level of imidazolinone-resistant ALS activity was observed in the transformants to a concentration of 1 mM imazapyr. Transformant 435-3A showed slightly higher ALS activity than the transformants 435-8A. These results correlate well with the leaf cutting assay.

To ascertain the reliability of the data, plants were transformed with the vector only (409-H1). The 409-H1 vector is a transformed plant vector with the pTRA409 plant transformation vector, but absent the mutant ALS gene used in the construction of the expression vector. As seen in FIG. 6, 409-H1 vector transformed plants showed essentially the same levels of inhibition as the non-transformed plant when exposed to various concentrations of imazapyr. Therefore, the imazapyr resistance in the transgenic plants was due to the introduced mutant ALS gene, and not a result of an artifact of the shuttle vector.

Applications of the Herbicide Resistance Among Transgenic Plants

By following the above procedures, plants can be obtained which are imidazolinone-resistant and can be grown in the field in the presence of imidazolinone without significant adverse effect on their growth.

The subject invention provides for the improvement of plants by making them herbicide resistant, particularly to specific imidazolinone herbicides. Thus, the gene encoding for imidazolinone-resistant ALS can be introduced into a plant host, whereby the gene will be expressed and impart imidazolinone-resistance to the plant. The mutant ALS gene can be introduced into other crop species to develop imidazolinone-resistant crop varieties. Also, similar mutations can be introduced at the corresponding nucleotide positions of other ALS genes to confer imidazolinone resistance. This mutant gene can also be used as a selection marker in plant transformation systems with its native promoter in dicots and with a modified promoter in monocots.

Moreover, this gene could be expressed in prokaryotic systems in conjunction with site-directed mutagenesis to study the mechanisms by which different groups of herbicides inhibit ALS. Alternatively, the system could be used to characterize the sites involved in feed back regulation, catalysis, and herbicide binding.

Deposits of the expression vector plasmid pTRA435 (ATCC 40978) and subclone pKS1 (ATCC 40977) each containing the mutant acetolactate gene from *Arabidopsis thaliana*, and the transgenic plant seeds of pTRA435-3A (ATCC 40979) have been made with the American Type Culture Collection at 12301 Parklawn Drive, Rockville, Md. 20852. The expression vector and the subclone containing the mutant imidazolinone-resistant ALS gene, and the resultant transgenic plant seeds have been given identifying numbers,(ATCC 40978) and (ATCC 40977) and (ATCC 40797) respectively. These specimens, on patenting will be maintained on deposit for a period of thirty years, for five years after the last request for a specimen, or for the enforceable life of the patent, whichever is longer. Should the deposits become nonviable they will be replaced. Assurance of access to the deposits as determined by the Commissioner under 37 CFR 1.14 is provided for cell restrictions on the availability of the deposits to the public-will-be irrevocably removed on the granting of a patent.

Although the foregoing invention has been described in some detail by way of illustration and example for purposes of clarity and understanding, it will be obvious that certain changes and modifications may be practiced within the scope of the appended claims without departing from the spirit and scope of the invention.

What is claimed is:

1. A bacterium which comprises a foreign nucleic acid encoding an imidazolinone-resistant acetolactate synthase, wherein said nucleic acid has the nucleotide sequence of FIG. 1 of the specification set forth as SEQ ID NO: 1.

2. The bacterium according to claim 1, wherein said bacterium is Agrobacterium.

3. A bacterium having a foreign nucleic acid which encodes a polypeptide comprising the amino acid sequence depicted in FIG. 1 (SEQ ID NO: 2).

4. The bacterium according to claim 3, wherein said bacterium is Agrobacterium.

5. A bacterium transformed with a vector containing a nucleotide sequence that encodes a polypeptide comprising the amino acid sequence depicted in FIG. 1 (SEQ ID NO: 2).

6. A bacterium according to claim 5 wherein said bacterium is Agrobacterium.

7. A bacterium according to claim 6 wherein said Agrobacterium is transformed with a Ti plasmid containing said nucleotide sequence.

8. A bacterium according to claim 7, wherein said nucleotide sequence is inserted into T-DNA or said Ti plasmid.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 2365 base pairs
        (B) TYPE: nucleic acid
        (C) STRANDEDNESS: double
        (D) TOPOLOGY: linear     (ii) MOLECULE TYPE: DNA (genomic)

(xi) SEQUENCE DESCRIPTION: SEQ ID NO:1:

```
CTTGTATCCA TTCTCTTAAC CAATAAAAAA AGAAAGAAAG ATCAATTTGA TAAATTTCTC      60

AGCCACAAAT TCTACATTTA GGTTTTAGCA TATCGAAGGC TCAATCACAA ATACAATAGA     120

TAGACTAGAG ATTCCAGCGT CACGTGAGTT TTATCTATAA ATAAAGGACC AAAAATCAAA     180

TCCCGAGGGC ATTTTCGTAA TCCAACATAA AACCCTTAAA CTTCAAGTCT CATTTTTAAA     240

CAAATCATGT TCACAAGTCT CTTCTTCTTC TCTGTTTCTC TATCTCTTGC TCATCTTTCT     300

CCTGAACCAT GGCGGCGGCA ACAACAACAA CAACAACATC TTCTTCGATC TCCTTCTCCA     360

CCAAACCATC TCCTTCCTCC TCCAAATCAC CATTACCAAT CTCCAGATTC TCCCTCCCAT     420

TCTCCCTAAA CCCCAACAAA TCATCCTCCT CCTCCCGCCG CCGCGGTATC AAATCCAGCT     480

CTCCCTCCTC CATCTCCGCC GTGCTCAACA CAACCACCAA TGTCACAACC ACTCCCTCTC     540

CAACCAAACC TACCAAACCC GAAACATTCA TCTCCCGATT CGCTCCAGAT CAACCCCGCA     600

AAGGCGCTGA TATCCTCGTC GAAGCTTTAG AACGTCAAGG CGTAGAAACC GTATTCGCTT     660

ACCCTGGAGG TGCATCAATG GAGATTCACC AAGCCTTAAC CCGCTCTTCC TCAATCCGTA     720

ACGTCCTTCC TCGTCACGAA CAAGGAGGTG TATTCGCAGC AGAAGGATAC GCTCGATCCT     780

CAGGTAAACC AGGTATCTGT ATAGCCACTT CAGGTCCCGG AGCTACAAAT CTCGTTAGCG     840
```

```
GATTAGCCGA TGCGTTGTTA GATAGTGTTC CTCTTGTAGC AATCACAGGA CAAGTCCCTC      900

GTCGTATGAT TGGTACAGAT GCGTTTCAAG AGACTCCGAT TGTTGAGGTA ACGCGTTCGA      960

TTACGAAGCA TAACTATCTT GTGATGGATG TTGAAGATAT CCCTAGGATT ATTGAGGAAG     1020

CTTTCTTTTT AGCTACTTCT GGTAGACCTG GACCTGTTTT GGTTGATGTT CCTAAAGATA     1080

TTCAACAACA GCTTGCGATT CCTAATTGGG AACAGGCTAT GAGATTACCT GGTTATATGT     1140

CTAGGATGCC TAAACCTCCG GAAGATTCTC ATTTGGAGCA GATTGTTAGG TTGATTTCTG     1200

AGTCTAAGAA GCCTGTGTTG TATGTTGGTG GTGGTTGTTT GAATTCTAGC GATGAATTGG     1260

GTAGGTTTGT TGAGCTTACG GGGATCCCTG TTGCGAGTAC GTTGATGGGG CTGGGATCTT     1320

ATCCTTGTGA TGATGAGTTG TCGTTACATA TGCTTGGAAT GCATGGGACT GTGTATGCAA     1380

ATTACGCTGT GGAGCATAGT GATTTGTTGT TGGCGTTTGG GGTAAGGTTT GATGATCGTG     1440

TCACGGGTAA GCTTGAGGCT TTTGCTAGTA GGGCTAAGAT TGTTCATATT GATATTGACT     1500

CGGCTGAGAT TGGGAAGAAT AAGACTCCTC ATGTGTCTGT GTGTGGTGAT GTTAAGCTGG     1560

CTTTGCAAGG GATGAATAAG GTTCTTGAGA ACCGAGCGGA GGAGCTTAAG CTTGATTTTG     1620

GAGTTTGGAG GAATGAGTTG AACGTACAGA AACAGAAGTT TCCGTTGAGC TTTAAGACGT     1680

TTGGGGAAGC TATTCCTCCA CAGTATGCGA TTAAGGTCCT TGATGAGTTG ACTGATGGAA     1740

AAGCCATAAT AAGTACTGGT GTCGGGCAAC ATCAAATGTG GGCGGCGCAG TTCTACAATT     1800

ACAAGAAACC AAGGCAGTGG CTATCATCAG GAGGCCTTGG AGCTATGGGA TTTGGACTTC     1860

CTGCTGCGAT TGGAGCGTCT GTTGCTAACC CTGATGCGAT AGTTGTGGAT ATTGACGGAG     1920

ATGGAAGCTT TATAATGAAT GTGCAAGAGC TAGCCACTAT TCGTGTAGAG AATCTTCCAG     1980

TGAAGGTACT TTTATTAAAC AACCAGCATC TTGGCATGGT TATGCAATGG GAAGATCGGT     2040

TCTACAAAGC TAACCGAGCT CACACATTTC TCGGGGATCC GGCTCAGGAG GACGAGATAT     2100

TCCCGAACAT GTTGCTGTTT GCAGCAGCTT GCGGGATTCC AGCGGCGAGG GTGACAAAGA     2160

AAGCAGATCT CCGAGAAGCT ATTCAGACAA TGCTGGATAC ACCAGGACCT TACCTGTTGG     2220

ATGTGATTTG TCCGCACCAA GAACATGTGT TGCCGATGAT CCCGAATGGT GGCACTTTCA     2280

ACGATGTCAT AACGGAAGGA GATGGCCGGA TTAAATACTG AGAGATGAAA CCGGTGATTA     2340

TCAGAACCTT TTATGGTCTT TGTAT                                          2365
```

(2) INFORMATION FOR SEQ ID NO:2:

(i) SEQUENCE CHARACTERISTICS:
        (A) LENGTH: 670 amino acids
        (B) TYPE: amino acid
        (D) TOPOLOGY: linear     (ii) MOLECULE TYPE: peptide     (xi) SEQUENCE DESCRIPTION: SEQ ID NO:2:

```
Met Ala Ala Ala Thr Thr Thr Thr Thr Ser Ser Ser Ile Ser Phe
1               5                  10                  15

Ser Thr Lys Pro Ser Pro Ser Ser Lys Ser Pro Leu Pro Ile Ser
                20                  25                  30

Arg Phe Ser Leu Pro Phe Ser Leu Asn Pro Asn Lys Ser Ser Ser
            35                  40                  45

Ser Arg Arg Arg Gly Ile Lys Ser Ser Ser Pro Ser Ser Ile Ser Ala
        50                  55                  60

Val Leu Asn Thr Thr Thr Asn Val Thr Thr Pro Ser Pro Thr Lys
65                  70                  75                  80
```

-continued

```
Pro Thr Lys Pro Glu Thr Phe Ile Ser Arg Phe Ala Pro Asp Gln Pro
             85                  90                  95

Arg Lys Gly Ala Asp Ile Leu Val Glu Ala Leu Glu Arg Gln Gly Val
            100                 105                 110

Glu Thr Val Phe Ala Tyr Pro Gly Gly Ala Ser Met Glu Ile His Gln
            115                 120                 125

Ala Leu Thr Arg Ser Ser Ile Arg Asn Val Leu Pro Arg His Glu
130                 135                 140

Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Gly Ala Thr Asn Leu Val
                165                 170                 175

Ser Gly Leu Ala Asp Ala Leu Leu Asp Ser Val Pro Leu Val Ala Ile
                180                 185                 190

Thr Gly Gln Val Pro Arg Arg Met Ile Gly Thr Asp Ala Phe Gln Glu
            195                 200                 205

Thr Pro Ile Val Glu Val Thr Arg Ser Ile Thr Lys His Asn Tyr Leu
210                 215                 220

Val Met Asp Val Glu Asp Ile Pro Arg Ile Ile Glu Glu Ala Phe Phe
225                 230                 235                 240

Leu Ala Thr Ser Gly Arg Pro Gly Pro Val Leu Val Asp Val Pro Lys
                245                 250                 255

Asp Ile Gln Gln Gln Leu Ala Ile Pro Asn Trp Glu Gln Ala Met Arg
            260                 265                 270

Leu Pro Gly Tyr Met Ser Arg Met Pro Lys Pro Pro Glu Asp Ser His
            275                 280                 285

Leu Glu Gln Ile Val Arg Leu Ile Ser Glu Ser Lys Lys Pro Val Leu
290                 295                 300

Tyr Val Gly Gly Gly Cys Leu Asn Ser Ser Asp Glu Leu Gly Arg Phe
305                 310                 315                 320

Val Glu Leu Thr Gly Ile Pro Val Ala Ser Thr Leu Met Gly Leu Gly
                325                 330                 335

Ser Tyr Pro Cys Asp Asp Glu Leu Ser Leu His Met Leu Gly Met His
                340                 345                 350

Gly Thr Val Tyr Ala Asn Tyr Ala Val Glu His Ser Asp Leu Leu Leu
            355                 360                 365

Ala Phe Gly Val Arg Phe Asp Asp Arg Val Thr Gly Lys Leu Glu Ala
370                 375                 380

Phe Ala Ser Arg Ala Lys Ile Val His Ile Asp Ile Asp Ser Ala Glu
385                 390                 395                 400

Ile Gly Lys Asn Lys Thr Pro His Val Ser Val Cys Gly Asp Val Lys
                405                 410                 415

Leu Ala Leu Gln Gly Met Asn Lys Val Leu Glu Asn Arg Ala Glu Glu
            420                 425                 430

Leu Lys Leu Asp Phe Gly Val Trp Arg Asn Glu Leu Asn Val Gln Lys
            435                 440                 445

Gln Lys Phe Pro Leu Ser Phe Lys Thr Phe Gly Glu Ala Ile Pro Pro
            450                 455                 460

Gln Tyr Ala Ile Lys Val Leu Asp Glu Leu Thr Asp Gly Lys Ala Ile
465                 470                 475                 480

Ile Ser Thr Gly Val Gly Gln His Gln Met Trp Ala Ala Gln Phe Tyr
                485                 490                 495

Asn Tyr Lys Lys Pro Arg Gln Trp Leu Ser Ser Gly Gly Leu Gly Ala
```

```
                    500                     505                     510
Met Gly Phe Gly Leu Pro Ala Ala Ile Gly Ala Ser Val Ala Asn Pro
            515                     520                     525

Asp Ala Ile Val Val Asp Ile Asp Gly Asp Gly Ser Phe Ile Met Asn
        530                     535                     540

Val Gln Glu Leu Ala Thr Ile Arg Val Glu Asn Leu Pro Val Lys Val
545                     550                     555                     560

Leu Leu Leu Asn Asn Gln His Leu Gly Met Val Met Gln Trp Glu Asp
                565                     570                     575

Arg Phe Tyr Lys Ala Asn Arg Ala His Thr Phe Leu Gly Asp Pro Ala
            580                     585                     590

Gln Glu Asp Glu Ile Phe Pro Asn Met Leu Leu Phe Ala Ala Ala Cys
            595                     600                     605

Gly Ile Pro Ala Ala Arg Val Thr Lys Lys Ala Asp Leu Arg Glu Ala
            610                     615                     620

Ile Gln Thr Met Leu Asp Thr Pro Gly Pro Tyr Leu Leu Asp Val Ile
625                     630                     635                     640

Cys Pro His Gln Glu His Val Leu Pro Met Ile Pro Asn Gly Gly Thr
                645                     650                     655

Phe Asn Asp Val Ile Thr Glu Gly Asp Gly Arg Ile Lys Tyr
                660                     665                     670
```